United States Patent [19]

Kimura et al.

[11] Patent Number: 4,691,060
[45] Date of Patent: Sep. 1, 1987

[54] PROCESS FOR RECOVERING WASTE HEAT FROM FORMALDEHYDE PRODUCT GAS

[75] Inventors: Shigeo Kimura, Nagoya; Kouichi Kurata, Mie, both of Japan

[73] Assignee: Mitsubishi Gas Chemical Company, Inc., Tokyo, Japan

[21] Appl. No.: 931,990

[22] Filed: Nov. 25, 1986

Related U.S. Application Data

[63] Continuation of Ser. No. 825,767, Feb. 3, 1986, abandoned, which is a continuation of Ser. No. 669,174, Nov. 7, 1984.

[51] Int. Cl.⁴ ............................................. C07C 47/052
[52] U.S. Cl. .................................... 568/420; 568/471; 568/493
[58] Field of Search .................... 568/420, 493, 471

[56] References Cited

U.S. PATENT DOCUMENTS

| | | | |
|---|---|---|---|
| 3,151,960 | 10/1964 | Roois | 568/493 X |
| 4,358,623 | 11/1982 | Murphy et al. | 568/471 X |
| 4,450,301 | 5/1984 | McMillan et al. | 568/471 X |

FOREIGN PATENT DOCUMENTS

| | | |
|---|---|---|
| 20527 | 6/1973 | Japan . |
| 101312 | 2/1975 | Japan . |
| 3015306 | 2/1978 | Japan . |
| 15307 | 2/1978 | Japan . |
| 55-11653 | 3/1980 | Japan . |

Primary Examiner—John E. Kittle
Assistant Examiner—Mukund J. Shah
Attorney, Agent, or Firm—Armstrong, Nikaido, Marmelstein & Kubovcik

[57] ABSTRACT

Waste heat possessed by a hot formaldehyde product gas obtained by catalytic reaction of methanol with air is heat exchanged with pressurized water in a waste heat boiler, thereby generating steam, and then leading the product gas to a formaldehyde absorption column, thereby absorbing formaldehyde, into an aqueous solution, and heat exchanging a recycling solution for a feed gas humidifier with the aqueous solution withdrawn from the bottom of absorption column. The waste heat can be efficiently recovered without deposition of paraformaldehyde on the heat transfer surface of heat exchanger and the amount of additional steam can be reduced or made entirely zero.

3 Claims, 1 Drawing Figure

PROCESS FOR RECOVERING WASTE HEAT FROM FORMALDEHYDE PRODUCT GAS

This application is a continuation of application Ser. No. 825,767 filed Feb. 3, 1986, now abandoned, which is a continuation of application Ser. No. 669,174 filed 11784.

BACKGROUND OF THE INVENTION

This invention relates to a process for recovering waste heat from formaldehyde product gas obtained by catalytic reaction of methanol with air.

Reaction of methanol with air in the presence of a silver catalyst to produce formaldehyde according to the so called methanol excess process consists of an endothermic reaction based on dehydrogenation of methanol and an exothermic reaction based on reaction of the resulting hydrogen with the oxygen in the feed air to produce water, and is, on the whole, an exothermic reaction.

Usually, the catalytic reaction of methanol with air in a commercial scale apparatus is carried out by mixing methanol vapor, preheated air and additional steam in a predetermined proportion, introducing the mixture to a reactor and conducting the reaction in the presence of a silver catalyst at a temperature of 550° to 700° C. The formaldehyde contained in the reaction product gas will be decomposed at an elevated temperature in that case, and thus the product gas is immediately quenched to 120° to 200° C. in a waste heat boiler through heat exchange with pressurized water, and then is introduced into an absorption column.

Since the formaldehyde-forming reaction is a reaction to by-produce water, a two-stage absorption column comprising a packed section as a lower stage and a bubble-capped section as an upper stage is generally used as the absorption column from the viewpoints of water balance and absorption efficiency. The aqueous formaldehyde solution withdrawn from the lower stage of the absorption column is cooled by cooling water, etc. in a heat exchanger, and returned to the absorption column. That is, the sensible heat and latent heat of the product gas are not usually recovered and are discharged in the form of waste warm water.

To utilize the heat possessed by the formaldehyde product gas, processes for recovering it as a heat source for concentrating formaldehyde or for removing unreacted methanol from the product gas have been proposed [Japanese Patent Publications Nos. 34-6718 and 48-20527, and Japanese Patent Application Kokai (Laid-open) No. 49-101312]. However, any of these processes is not satisfactory in the effective utilization of the heat possessed by the formaldehyde product gas. To make more effective utilization, processes for recovering it as a heat source for vaporizing methanol have been also proposed (Japanese Patent Publications Nos. 5511653 and 55-30783).

Recent needs for the product formaldehyde have a tendency toward a higher formaldehyde concentration and a lower methanol concentration. For example, the conventional product has 37% by weight of formaldehyde and 2 to 7% by weight of unreacted methanol, whereas the recent needs for the product formaldehyde are 40 to 55% by weight of formaldehyde and 1 to 5% by weight of unreacted methanol. To meet such needs, it is necessary to select a higher air-to-methanol ratio for a feed gas mixture. To use such a higher air-to-methanol ratio, it is necessary to narrow the explosion limit of an air-methanol gas mixture, and one of the measures is addition of an inert gas such as steam, etc. to the air-methanol gas mixture. However, the amount of such additional inert gas, such as steam, must be increased with enhanced reactivity.

An increasing amount of the additional steam will impair the unit consumption of steam for the production of formaldehyde, and also the direct addition of steam to the reaction system will be a possible cause for fouling the catalyst because of deposition of involatile matters entrained by steam from steam steel pipings. Thus, the amount of additional steam is desirably as small as possible.

SUMMARY OF THE INVENTION

An object of the present invention is to overcome the disadvantages of the prior art by directly contacting a non-condensible gas as a feed gas with heated water, thereby humidifying the feed gas, while utilizing the heat possessed by the formaldehyde product gas as a heat source for heating the water.

According to the present invention, a product gas containing formaldehyde, obtained by catalytic oxidationdehydrogenation reaction of methanol with air is heat exchanged with pressurized water in a waste heat boiler to generate steam, and then introduced into formaldehyde absorption column, while heating a recycling water for a feed gas humidifer with an aqueous formaldehyde recycling solution withdrawn from the bottom of the absorption column.

According to the present invention, a portion or the whole amount of 0.2 to 2.0 moles of steam to be mixed with one mole of methanol in the ordinary feed gas mixture for producing formaldehyde in the methanol excess process can be saved. This means that it is possible to reduce 50 to 320 kg of steam necessary for producing 1 metric ton of an aqueous formaldehyde solution in terms of 37.0% by weight of formaldehyde to entirely zero, and, furthermore, the excess steam can be supplied to other facility from the formaldehyde-producing facility.

The aqueous formaldehyde solution produced in the methanol excess process usually contains 37 to 55% by weight of formaldehyde and 1 to 7% by weight of methanol, and the feed gas mixture can be usually prepared by mixing methanol vapors evaporated at a predetermined flow rate in a methanol evaporator with preheated air and steam, and introduced into a reactor.

The feed gas mixture usually has a ratio by mole of methanol: air: steam of 1:1.3–2.0: 0.2–2.0. After the reaction, the product gas cooled to 120° to 200° C. in a waste heat boiler usually contains 20 to 26% by mole of formaldehyde, 1 to 4% by mole of methanol, 28 to 40% by mole of steam, and 40 to 46% by mole of non-condensible gas such as $H_2$, $N_2$, $CO$, $CO_2$, etc. as the balance. The product gas has a dew point of 80° to 85° C., and in recovering the waste heat from the product gas, it is naturally advantageous to cool the product gas to a temperature below the dew point where the condensation starts, and recover both the sensible heat and the heat of condensation of the product gas. However, cooling of the product gas to a temperature below dew point will deposit paraformaldehyde, polymer of formaldehyde, on the heat transfer surface of heat exchanger, not only lowering the heat transfer effect, but also causing cloggings within the apparatus, thus posing serious problems on the product itself. Thus, to prevent paraformaldehyde deposition, it is the ordinary expedient to recover only the sensible heat and not the latent heat when the waste heat is recovered through a heat exchanger directly from the product gas leaving the waste heat boiler.

To recover the latent heat, in the present invention, the product gas leaving the waste heat boiler is subjected to absorption in an absorption column to obtain an aqueous formaldehyde solution, and then the heat of absorption is recovered from the aqueous formaldehyde solution through a heat exchanger in place of the direct heat exchange of the product gas leaving the waste heat boiler. In the present invention, the waste heat can be effectively recovered without deposition of paraformaldehyde.

BRIEF DESCRIPTION OF THE DRAWING

Single Figure is a flow diagram showing the steps of the present invention.

PREFERRED EMBODIMENTS OF THE INVENTION

Figure 1:
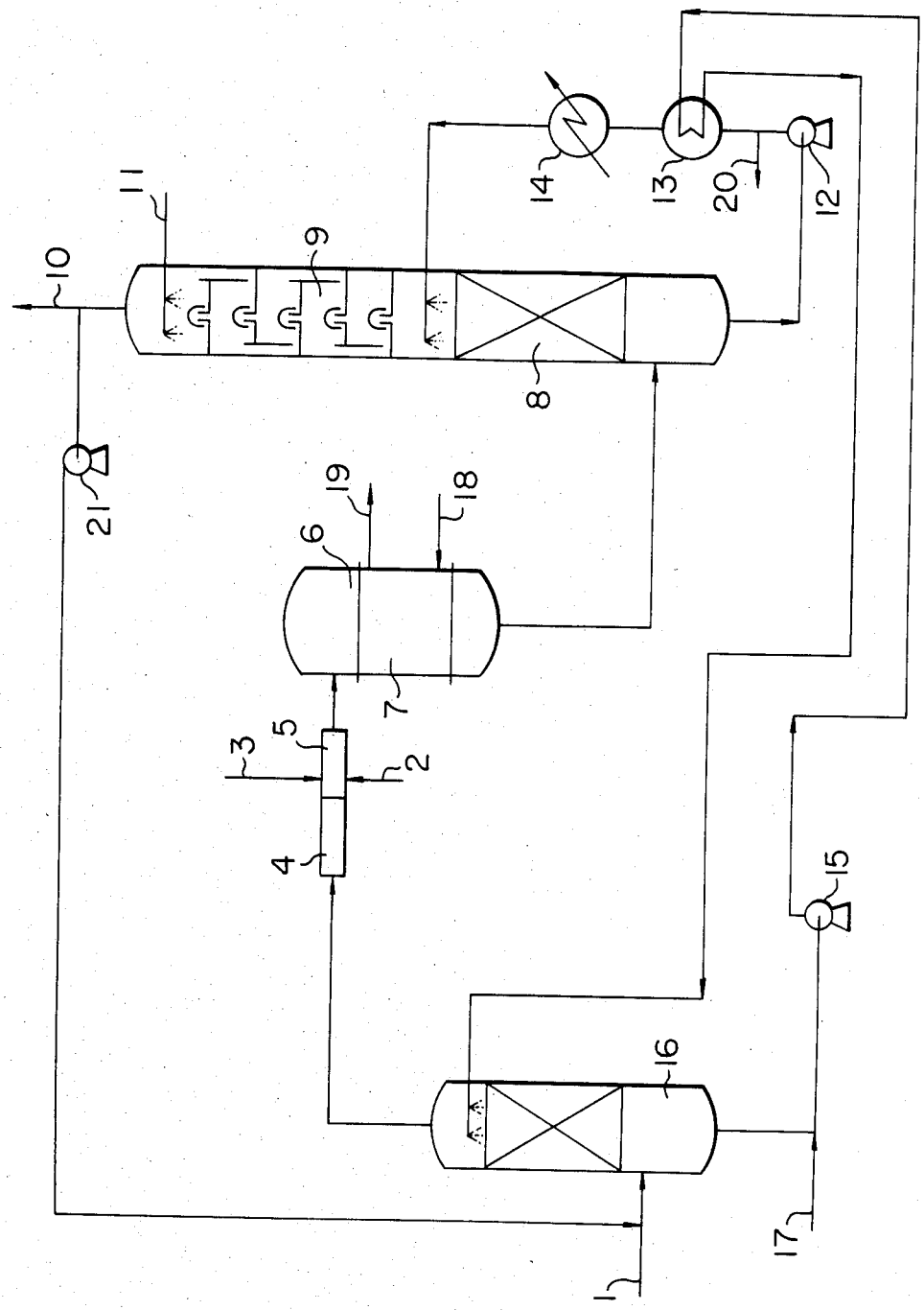

The present invention will be described below, referring to the flow diagram shown in Figure.

At the start of operation, the heat possessed by the product gas is little, and the operation is thus not in a stable state. In that case, humidifier 16 is thus not operated and feed air is led to preheater 4 from line 1 while passing humidifier 16, and preheated in preheater 4.

Feed methanol vapor is fed to a gas mixer 5 from line 2 and feed steam, if necessary, is fed also thereto from line 3, and they are mixed in gas mixer 5. The resulting mixture is led to reactor 6.

The formaldehyde product gas leaving reactor 6 is immediately heat exchanged with pressurized water 18 in waste heat boiler 7 to generate steam 19, whereas the product gas itself is cooled to 120° to 200° C., and then led to packed section 8 of formaldehyde absorption column. The formaldehyde unabsorbed in packed section 8 is further contacted with deionized water 11 in bubble-capped section 9 of absorption column and subjected to further absorption therein. Non-condensible gas is vented through line 10 as waste gas, a portion of which is recycled to the starting material line 1 by blower 21.

The aqueous formaldehyde solution withdrawn from the bottom of absorption column is pressurized by pump 12, cooled through heat exchanger 14, and then returned to the top of packed section of absorption column, and mixed and diluted with the dilute formaldehyde solution leaving the bubble-capped section 9. The solution mixture enters packed section 8 to absorb formaldehyde in the formaldehyde product gas again. Product aqueous formaldehyde solution having a desired concentration thus obtained is withdrawn through line 20.

After the operation has been stabilized, the operating procedure is switched to that of the present invention. At first, recyling pump 15 for the bottom solution of humidifier 16 is started to supply make-up water for humidifier 16 through line 17, and the recycle solution pressurized by pump 15 is heat exchanged with the recycling solution withdrawn from the bottom of packed section 8 of the formaldehyde absorption column through heat exchanger 13 and returned to the top of humidifier 16 and directly contacted with the feed gas by gas-liquid countercurrent to humidify the feed gas (air or air and vent gas).

The flow rate of water entrained by the feed air in humidifier 16 depends on the water temperature of the recycling solution returned to humidifier 16. Thus, the flow rate of cooling water through heat exchanger 14 is adjusted to make the temperature of heat exchanger 13 constant.

By conducting the foregoing operating procedure, the flow rate of water entrained by air or non-condensible gas can be adjusted as desired by the solution temperature in humidifier 16 and thus the amount of steam so far used as additional steam can be reduced or made entirely zero, whereby the object of the present invention can be attained.

The present invention will be described in detail below, referring to Examples.

EXAMPLE 1

A product aqueous formaldehyde solution was produced at a rate of 100 metric tons per day in terms of 37% by weight of formaldehyde in a system shown by the flow diagram in Figure.

Feed methanol was evaporated at a flow rate of 2,040 kg/hr in a methanol evaporator (not shown in the drawing) and led to mixer 5 from line 2. Feed air was supplied to humidifier 16 through line 1 at a flow rate of 2,860 $Nm^3$/hr. The recycling solution for humidifier 16 was adjusted to 70° C., and the feed air containing steam leaving humidifier 16 was led to preheater 4, preheated to 110° C., and mixed with the methanol vapor in mixer 5. The mixture was led to reactor 6.

The feed gas mixture at the inlet to reactor 6 had a ratio by mole of methanol:air:steam of 1:2.0:1.2 . The mixture was led to the reactor 6 and reaction was conducted on a silver catalyst bed at a temperature of 640° C. After the reaction, a product gas containing formaldehyde was heat exchanged with pressurized water in waste heat boiler 7, cooled to 140° C. and then led to the absorption column. The product gas was at first contacted with the recycling solution in packed section 8 as the lower stage of the absorption column and subjected to absorption into the recycling aqueous formaldehyde solution, and then contacted with deionized water in bubble-capped section as the upper stage of the absorption column and subjected to absorption into the deionized water, while venting remaining noncondensible gas from the top of the absorption column. The recycling solution for the absorption column was withdrawn from the bottom of the absorption column and pressurized by recycle pump 12, led at the flow rate of 120 $m^3$/hr and the temperature of 75° C. to heat exchanger 13 for heating the recycling water for humidifier 16, and then to heat exchanger 14 for cooling. The recycling aqueous formaldehyde solution for the absorption column thus cooled to 50° C. was returned to the top of packed section 8 of the absorption column.

On the other hand, the recycling water for humidifier 16 was pressurized by recycle pump 15, led to heat exchanger 13 for heating the recycling water for humidifier 16, heat exchanged with the recycling aqueous formaldehyde solution withdrawn from the formaldehyde absorption column and heated to 70° C., and returned to humidifier 16 for reuse.

As make-up water in the amount corresponding to that of the water entrained by the feed air as steam, deionized water was supplied to the suction side of recycle pump 15 for humidifier 16 through line 17 to stabilize the water level in humidifier 16.

Product aqueous formaldehyde solution was obtained from the absorption column at a flow rate of 3,700 kg/hr, and had a formaldehyde concentration of 45% by weight and methanol concentration of 2% by weight.

As a result of the foregoing operation, 1,000 kg/hr of steam so far used as the feed steam, which corresponded to 220 kg per 1,000 kg of product aqueous formaldehyde solution in terms of 37% by weight of formaldehyde, could be completely saved. This excess steam as saved could be supplied to other facility from the formaldehyde production system. As a result of inspection of heat exchanger 13 for heating the recycling water for humidifier 16 one year after the operation, no deposition of paraformaldehyde was observed on the heat transfer surface.

EXAMPLE 2

Operation was conducted in the same manner as in Example 1 according to the flow diagram in Figure, except that a portion of the vent gas through line 10 was mixed into the feed air by blower 21 for vent gas recycling. That is, feed methanol flow rate was 1,700 kg/hr, and feed air flow rate was 2,380 Nm³/hr. A portion of vent gas discharged from the top of the formaldehyde absorption column was mixed at a flow rate of 1,190 Nm³/hr with the feed air and fed tc humidifier 16.

The feed gas mixture at the inlet to reactor 6 had a ratio by mole of methanol: air: steam: vent gas of 1:2.0:1.28:1.0.

Silver catalyst bed in reactor 6 was at 660° C., and after the reaction, a product gas containing formaldehyde was heat exchanged with pressurized water in waste heat boiler 7, cooled to 150° C. and then subjected to the same operations as in Example 1.

As a result, a product aqueous formaldehyde solution was obtained at a rate of 2,540 kg/hr, and had a formaldehyde concentration of 55% by weight and a methanol concentration of 1.5% by weight.

As a result of the foregoing operation, 1,220 kg/hr of steam so far used as the feed steam, which corresponded to 325 kg of steam per 1,000 kg of product aqueous formaldehyde solution in terms of 37% by weight of formaldehyde, could be completely saved.

As a result of inspecting heat exchanger 13 for heating the recycling water for humidifier one year after the operation, no deposition of paraformaldehyde was observed on the heat transfer surface.

What is claimed is:

1. A process for producing formaldehyde which comprises reacting a feed gas mixture comprising methanol, steam and air in the presence of a silver catalyst; heat exchanging a resulting hot formaldehyde containing product gas with pressurized water in a waste heat boiler, thereby generating steam; flowing the product gas to a formaldehyde absorption column and absorbing formaldehyde into an aqueous solution at the bottom of the absorption column; heat exchanging the aqueous formaldehyde-containing solution with water, thereby obtaining hot water; and introducing the hot water and feed air into a feed gas humidifier, the heated water being introduced into the top of the gas humidifier to thereby contact the hot water with the feed air by a gas liquid countercurrent and vaporizing the hot water into the feed air.

2. A process according to claim 1, wherein the hot formaldehyde-containing product gas is cooled to a temperature above the dew point of the product gas in the waste heat boiler by the heat exchanging.

3. A process according to claim 1, wherein the feed gas mixture also comprises waste gas.

* * * * *

UNITED STATES PATENT AND TRADEMARK OFFICE
CERTIFICATE OF CORRECTION

PATENT NO. : 4,691,060
DATED : September 1, 1987
INVENTOR(S) : KIMURA et al

It is certified that error appears in the above-identified patent and that said Letters Patent is hereby corrected as shown below:

On the cover page, Item [30] should read:

-- Foreign Application Priority Data
Nov. 7, 1983 [JP]   Japan..................58-208686--.

Signed and Sealed this

Fifth Day of April, 1988

Attest:

DONALD J. QUIGG

*Attesting Officer*   *Commissioner of Patents and Trademarks*